United States Patent [19]

Sakamoto et al.

[11] Patent Number: 4,654,368
[45] Date of Patent: Mar. 31, 1987

[54] TRI-ORGANOTIN SILATRANE DERIVATIVES AND PESTICIDAL COMPOSITIONS, FUNGICIDES OR ANTIFOULING AGENTS COMPRISING SAID COMPOUNDS AS ACTIVE INGREDIENTS

[75] Inventors: Kazuhiko Sakamoto, Osaka; Toshiharu Nakatsuji, Sakai; Hideo Mototani, Minoo; Katsuzo Kamoshita, Osaka; Isamu Nakayama, Kawanishi; Toshiro Kato, Takarazuka, all of Japan

[73] Assignee: Nitto Kasei Co., Ltd., Osaka, Japan

[21] Appl. No.: 755,347

[22] Filed: Jul. 16, 1985

[30] Foreign Application Priority Data

Jul. 19, 1984 [JP] Japan ................. 59-150870

[51] Int. Cl.⁴ .................. A21C 3/04; A21C 11/16; C07F 7/22
[52] U.S. Cl. ........................ 514/493; 556/9; 106/15.05
[58] Field of Search ............... 556/9; 514/493; 106/15.05

[56] References Cited

U.S. PATENT DOCUMENTS

| | | | |
|---|---|---|---|
| 3,395,164 | 7/1968 | Leebrick | 556/9 |
| 3,901,930 | 8/1975 | Wirth et al. | 556/9 X |
| 4,048,206 | 9/1977 | Voronkov et al. | 556/405 |
| 4,160,846 | 7/1979 | Strunk et al. | 556/9 X |

Primary Examiner—Helen M. S. Sneed
Attorney, Agent, or Firm—Wenderoth, Lind & Ponack

[57] ABSTRACT

A tri-organotin silatrane derivative represented by the general formula (I)

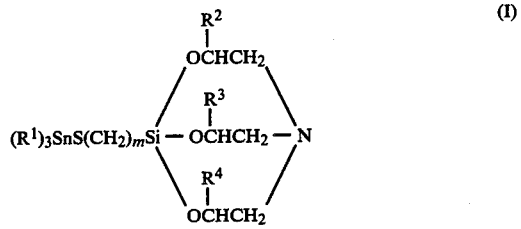

wherein the $R^1$ groups are identical or different and each represents an alkyl, cycloalkyl, aryl or aralkyl group, $R^2$, $R^3$ and $R^4$ are identical or different and each represents a hydrogen atom or a lower alkyl group, and m is a number of 2 or 3.

The tri-organotin silatrane derivatives of the formula (I) are prepared by subjecting a 1-mercaptoalkylsilatrane and a tri-organotin hydroxide or bis(tri-organotin) oxide to a dehydration reaction, or reacting a 1-mercaptoalkylsilatrane derivative with a tri-organotin halide in the presence of a dehydrohalogenation agent, or subjecting a trialkoxysilane and a trialkanolamine to an ester-interchange reaction in the presence of an alkaline catalyst.

The tri-organotin silatrane derivatives of the formula (I) are useful for an agricultural-horticultural pesticide, an industrial fungicide, an epidemic-preventing insecticide or an antifouling agent.

7 Claims, No Drawings

TRI-ORGANOTIN SILATRANE DERIVATIVES AND PESTICIDAL COMPOSITIONS, FUNGICIDES OR ANTIFOULING AGENTS COMPRISING SAID COMPOUNDS AS ACTIVE INGREDIENTS

This invention relates to tri-organotin silatrane derivatives, processes for production thereof, and pesticidal compositions and the like comprising these compounds as active ingredients. More specifically, this invention relates to tri-organotin silatrane derivatives containing sulfur, processes for production thereof, and pesticidal compositions, industrial fungicides, epidemic-preventing insecticides and antifouling agents containing such compounds as active ingredients.

Sulfur-containing organic silicon tin compounds of the following formula $$R_3Si(CH_2)_nSSnR'_3$$

wherein R represents an alkyl or alkoxy group, R' represents an alkyl group, and n is 1 or 3, have heretofore been known, and it is also known that these compounds are used to protect optical appliance parts from bacterial destruction (see USSR Pat. Nos. 638,558 and 777,039).

It is an object of this invention to provide novel tri-organotin silatrane derivatives.

Another object of this invention is to provide processes for producing these novel tri-organotin silatrane derivatives.

Still another object of this invention is to provide an agricultural-horticultural pesticidal composition comprising such a novel tri-organotin silatrane derivative.

Yet another object of this invention is to provide an industrial fungicide comprising such a novel tri-organotin silatrane derivative.

A further object of this invention is to provide an epidemic-preventing insecticide containing such a novel tri-organotin silatrane derivative.

An additional object of this invention is to provide an antifouling agent comprising such a novel tri-organotin silatrane derivative.

Other objects and advantages of this invention will become apparent from the following detailed description.

Firstly, these objects and advantages of this invention are achieved by a tri-organotin silatrane derivative represented by the general formula (I)

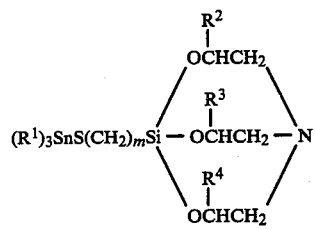

wherein the $R^1$ groups are identical or different and each represents an alkyl, cycloalkyl, aryl or aralkyl group, $R^2$, $R^3$ and $R^4$ are identical or different and each represents a hydrogen atom or a lower alkyl group, and m is a number of 2 or 3.

According to this invention, the compounds of general formula (I) can be produced by any one of the following three processes.

According to a first process, the compounds of general formula (I) can be produced by subjecting a 1-mercaptoalkylsilatrane represented by the general formula (II)

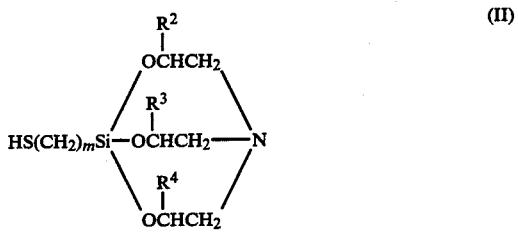

wherein $R^2$, $R^3$ and $R^4$ are identical or different and each represents a hydrogen atom or a lower alkyl group, and m is a number of 2 or 3, and a tri-organotin hydroxide or bis(tri-organotin)oxide represented by the general formula (III)

or

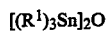

wherein $R^1$ groups are identical or different and each represents an alkyl, cycloalkyl, aryl or aralkyl group, to a dehydration reaction.

In formula (II), $R^2$, $R^3$ and $R^4$ are identical or different, and each represents a hydrogen atom or a lower alkyl group, and m is a number of 2 or 3. The lower alkyl group is, for example, a linear or branched alkyl group having 1 to 4 carbon atoms. Such lower alkyl groups include, for example, methyl, ethyl, n-propyl, isopropyl, n-butyl, iso-butyl, sec-butyl and t-butyl. Preferably, $R^2$, $R^3$ and $R^4$ are identical or different, and each represents a hydrogen atom or a methyl or ethyl group.

Among the 1-mercaptoalkylsilatranes of formula (II), the following three compounds are known [see J. Organometal. Chem., 233 (1982), pages 1–147].

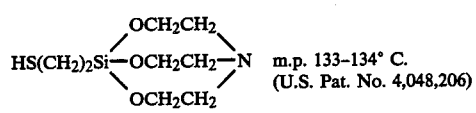 m.p. 133–134° C. (U.S. Pat. No. 4,048,206)

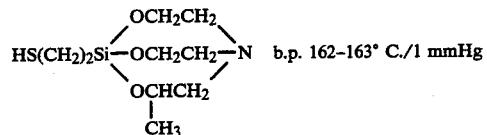 b.p. 162–163° C./1 mmHg

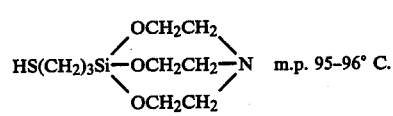 m.p. 95–96° C.

Others are novel compounds. These 1-mercaptoalkylsilatranes of formula (II) can be produced by reacting the corresponding mercaptoalkyltrialkoxysilanes and trialkanolamines in accordance with the method described in the above-cited publication.

The following compounds can, for example, be cited as examples of the compounds of formula (II).

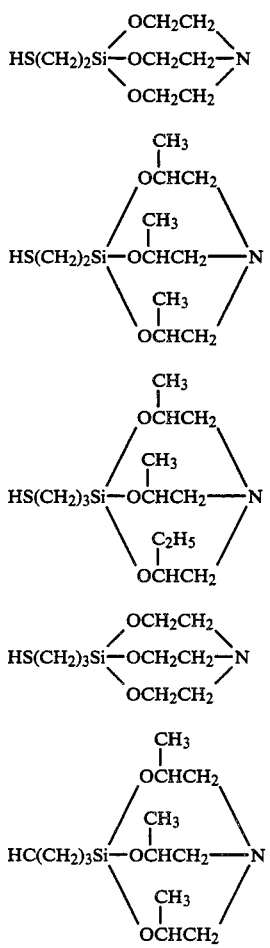

The three $R^1$ groups contained in the molecules in formula (III) are identical or different and each represents an alkyl, cycloalkyl, aryl or aralkyl group. The alkyl group is, for example, a linear or branched alkyl group having 1 to 8 carbon atoms. Examples of the alkyl group are methyl, ethyl, iso-propyl, n-propyl, n-butyl, iso-butyl, sec-butyl, t-butyl, n-pentyl, neo-pentyl, n-hexyl, n-heptyl and n-octyl. The cycloalkyl group is, for example, a cycloalkyl group having 5 to 8 carbon atoms. Specific examples include cyclopentyl, cyclohexyl, cycloheptyl and cyclooctyl. The aryl group is, for example, a phenyl, naphthyl, or biphenyl group. The aralkyl group is, for example, a phenyl alkyl group having 7 to 10 carbon atoms such as benzyl, phenethyl, 2- or 3-phenylpropyl or 2,2-dimethyl-2-phenylethyl.

Preferably, the three $R_1$ groups in the molecule in formula (III) are linear or branched propyl, butyl, pentyl, octyl, cyclohexyl, phenyl, and 2,2-dimethyl-2-phenylethyl.

Examples of the compound of formula (III) include trimethyltin hydroxide, tricyclohexyltin hydroxide, triphenyltin hydroxide, bis(triethyltin)oxide, bis(tri-n-propyltin)oxide, bis(tri-n-butyltin)oxide, bis(tri-neopentyltin)oxide, bis(tri-n-octyltin)oxide and bis(trineophyltin)oxide.

The reaction between the 1-mercaptoalkylsilatrane of formula (II) and the tri-organotin hydroxide or bis(tri-organotin)oxide of formula (III) can be carried out in the presence or absence of a solvent. The resulting water can be removed as an azeotrope with the solvent, or by dehydration under reduced pressure.

Usually, benzene, toluene, xylene, n-hexane, cyclohexane, n-heptane, and alcohols, for example, can be used as the solvent.

Usually, the compound of formula (II) and the tri-organotin hydroxide or bis(tri-organotin)oxide of formula (III) are used in stoichiometrical proportions, but their proportions are not necessarily limited to these.

There is no particular restriction on the reaction temperature. The reaction can be carried out at industrially advantageous temperatures, for example 30° to 150° C. To conduct the reaction smoothly, the reaction temperature is preferably the refluxing temperature of the solvent. The reaction is usually completed in 0.5 to 3 hours.

According to a second process, the compounds of formula (I) can be produced by reacting the 1-mercaptoalkylsilatrane of formula (II) given above with a tri-organotin halide represented by the general formula (IV)

$(R^1)_3SnX$             (IV)

wherein $R^1$ is defined as above, and X is a chlorine or bromine atom, in the presence of a dehydrohalogenation agent.

In formula (IV), the definition of $R^1$ is the same as in formula (I).

Examples of the compound of formula (IV) are trimethyltin chloride or bromide, triethyltin chloride or bromide, tri-n-propyltin chloride or bromide, tri-n-butyltin chloride or bromide, trioctyltin chloride or bromide, trineopentyltin chloride or bromide, ticyclohexyltin chloride or bromide, triphenyltin chloride or bromide and trineophyltin chloride or bromide.

Examples of the dehydrohalogenation agent are sodium hydroxide, potassium hydroxide, sodium ethoxide, sodium hydride, ammonia, triethylamine, tributylamine and pyridine.

The dehydrohalogenation agent may be added together with other reagents of the reaction system. When the dehydrohalogenation agent is an alkali metal compound, it may also be used in such a way that the 1-(mercaptoalkyl)silatrane derivative of general formula (II) is reacted with it to convert the silatrane derivative to a compound of the following formula (II)'

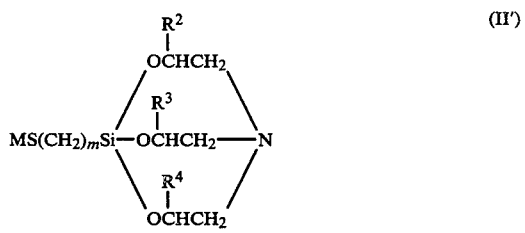

wherein $R^2$, $R^3$, $R^4$ and m are the same as defined hereinabove, and M represents an alkali metal atom.

The reaction may be carried out in the presence or absence of a solvent. Usually, it is carried out in the same solvent as exemplified above for the dehydration reaction in the presence of the dehydrohalogenation agent.

The mole ratio of the 1-(mercaptoalkyl)silatrane derivative of general formula (II) to the tri-organotin halide of formula (IV) is usually from 1:0.1 to 1:10, preferably from 1:1.0 to 1:1.2. The proportion of the dehydrogenation agent is at least 1.0 mole, preferably 1.0 to 1.5 mole, per mole of the 1-(mercaptoalkyl)silatrane derivative of general formula (II).

The reaction is completed usually in 0.5 to 3 hours at a temperature of, for example, 30° to 150° C.

According to a third process, the compound of formula (I) can be produced by subjecting a trialkoxysilane represented by the following formula (V)

$$(R^1)_3SnS(CH_2)_mSi(OR^5)_3 \qquad (V)$$

wherein $R^1$ and m are as defined hereinabove, and $R^5$ represents a lower alkyl group,
and a trialkanolamine represented by the general formula (VI)

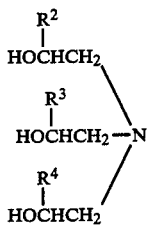

(VI)

wherein $R^2$, $R^3$ and $R^4$ are as defined hereinabove, to an ester-interchange reaction in the presence of an alkaline catalyst.

In formula (V), $R^1$ and m are the same as defined hereinabove, and $R^5$ is a lower alkyl group such as methyl, ethyl or propyl.

Examples of the trialkoxysilane of formula (V) in which $R^5$ is methyl are given below.

$(CH_3)_3SnS(CH_2)_2Si(OCH_3)_3$, $(C_2H_5)_3SnS(CH_2)_2Sn(OCH_3)_3$, $(C_3H_7)_3SnS(CH_2)_2Si(OCH_3)_3$, $(C_4H_9)_3SnS(CH_2)_2Sn((OCH_3)_3$, $(C_6H_5)_3SnS(CH_2)_3Sn(OCH_3)_3$, $(C_6H_{11})_3SnS(CH_2)_2Si(OCH_3)_3$, $(C_6H_5)_3SnS(CH_2)_2Sn(OCH_3)_3$, and $(neophyl)_3SnS(CH_2)_2Sn(OCH_3)_3$.

In formula (VI), the definitions of $R^2$, $R^3$ and $R^4$ are the same as given hereinabove.

Examples of the trialkanolamine represented by formula (VI) are given below.

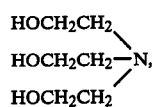

-continued

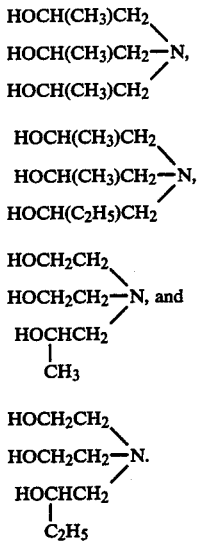

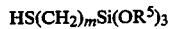

The reaction of the compounds of formulae (V) and (VI) can be carried out in the presence or absence of a solvent. The solvent is preferably benzene, toluene, xylene, n-hexane, cyclohexane or n-heptane.

The reaction is carried out in the presence of an alkaline catalyst such as sodium hydroxide, potassium hydroxide or sodium methylate.

The alcohol ($R^5OH$) formed by the reaction can be removed from the reaction system as an azeotrope with the reaction solvent, or under reduced pressure.

The trialkoxysilanes of formula (V) can be produced by subjecting a mercaptoalkyltrialkoxysilane represented by the following formula (VII)

$$HS(CH_2)_mSi(OR^5)_3 \qquad (VII)$$

wherein $R^5$ and m are as defined hereinabove, and the tri-organotin hydroxide or bis(tri-organotin)oxide of formula (III) to a dehydration reaction.

This dehydration reaction can be carried out in the presence or absence of a solvent. Water formed by the reaction can be removed as an azeotrope with the solvent, or by dehydration under reduced pressure.

The trialkoxysilane (V) so produced can usually be used directly as a starting material for the third process without isolating it, and this is advantageous.

In the reaction of the trialkoxysilane of formula (V) with the trialkanolamine of formula (VI) and the reaction of the mercaptoalkyltrialkoxysilane of formula (VII) with the compound of formula (III), the starting materials are used in stoichiometrical proportions, but these proportions are not limitative. Usually, the above reactions can be carried out at industrially advantageous temperatures, for example 30° to 150° C., and are completed usually in 0.5 to 3 hours.

In any of the first to third processes, the reaction mixture is worked up in a usual manner after the reaction, and if required, the desired product may be purified by recrystallization, treated with activated carbon, chromatography, etc.

The compounds of formula (I) in accordance with this invention are produced mainly by the three processes, but their production is by no means limited to them.

Thus, according to this invention, the compounds of formula (I) are provided.

In formula (I), $R^1$, $R^2$, $R^3$, $R^4$ and m are as defined hereinabove.

In formula (I), $R^1$ groups are identical or different, and are preferably alkyl groups having 1 to 8 carbon atoms, cycloalkyl groups having 5 to 8 carbon atoms, a phenyl group or phenylalkyl groups having 7 to 10 carbon atoms; $R^2$, $R^3$ and $R^4$ are identical or different and each represents a hydrogen atom or an alkyl group having 1 to 4 carbon atoms; and m is 2 or 3.

In formula (I), $R^1$ is especially preferably propyl, butyl, pentyl, octyl, cyclohexyl, phenyl or 2,2-dimethyl-2-phenylethyl, and $R^2$, $R^3$ or $R^4$ especially preferably represents a hydrogen atom or a methyl or ethyl group.

Many specific examples of the compounds of formula (I) are shown in Examples 1 to 4 below.

The compounds of this invention have an excellent fungicidal efficacy on filamentous fungi which are parasitic on agricultural and horticultural crops and exert harmfull actions, such as blast (*Piricularia oryzae* Cavara) and sheath blight (*Pillicularia sasakii*) of rice, late blight (*Phytophthora infestans*) of tomato, downy mildew (*Pseudoperonospora cubensis*) of cucumber, and powdery mildew (*Erysiphe graminis*) of barley and wheat, and can protect the crops from these pathogens.

The compounds of this invention also have a strong fungicidal effect against other molds, and can protect industrial products from molds and bacteria.

The compounds of this invention also have excellent pesticidal effects on noxious insects parasitic on agricultural and horticultural crops, such as armyworms and lavrae of lepidopterus insects, Tetranychus, *Panonychus ulmi*, and Panonychus parasitic on fruit trees, vegetables and flowers, and also pests injurious to human and animal health, such as larvae of mosquitoes and houseflies, and can protect agricultural and horticultural crops from these pests, and humans and domestic animals form these pests.

In addition, the compounds of this invention have an excellent antifouling effect against marine organisms which adhere to ships, underwater structures, fish nets for cultivation and which do harm to such structures. Examples are those such as barnacles, Serpulae, oysters, ascidians, green algae (Chlorophyceae), brown algae (Phaeophycedae) and diatoms (Bicillariophyceae), and the compounds can protect the ships, underwater structures, cultivation fish nets from these fouling organisms.

Accordingly, the compounds of this invention can be used as agricultural-horticultural insecticides, miticides and fungicides, industrial fungicides, epidemic-preventing insecticides and antifouling agents under water.

The compounds of this invention may be used directly without any other ingredient when it is desired to use them as insecticidal, miticidal or fungicidal agents. If desired, they may be formulated into oils, aerosols, etc. by mixing with solid carriers, liquid carriers surface-active agents and auxiliary compounds.

These formulations contain the compounds of this invention as active ingredients in a proportion of 0.1 to 99.9% by weight, preferably 2 to 80% by weight.

Examples of the solid carriers include vegetable carriers (such as wheat flour, tobacco stalk powder, soybean powder, chestnut shell powder, wood flour, sawdust, wheat bran, bark powder, cellulose powder and residues left after extraction of plants), fibrous products (such as paper, paper boards, used clothes), crushed plastics, powders of clays (such as kaolin, clay, bentonite, acid clay, talcs, and other inorganic minerals such as pyrophillite, sericite, pumice, sulfur powder and activated carbon), and fine powders of chemical fertilizers (such as ammonium sulfate, ammonium phosphate, ammonium nitrate, urea and ammonium chloride).

Examples of the liquid carriers include water, alcohols (such as methanol and ethanol), ketones (such as acetone and methyl ethyl ketone), ethers (such as ethyl ether, dioxane, Cellosolve and tetrahydrofuran), aromatic hydrocarbons (gasoline, and kerosene), esters, nitriles, acid amides (such as methylformamide and dimethylacetamide), and halogenated hydrocarbons (such as dichloroethane, trichloroethylene and carbon tetrachloride).

Other additives include surface-active agents such as alkylsulfuric acid esters, alkylsulfonic acid salts, alkylarylsulfonic acid salts, polyethylene glycol ethers and polyhydric alcohol esters; stickers or dispersing agents such as casein, gelatin, starch powder, carboxymethyl cellulose, gum arabic, alginic acid, lignin sulfonate, bentonite, molasses, polyvinyl alcohol, agar and turpentine oil; and stabilizers such as PAP (acidic isopropyl phosphate), TCP (tricresyl phosphate), tall oil, epoxidized oil, various surfactants, various fatty acids and esters of the fatty acids.

The compounds of this invention may be used as mixtures with other fungicides, insecticides and miticides, nematocides, insect repellents, plant growth regulators, herbicides, fertilizers, soil conditioners, etc.

When a compound of this invention is used as an agricultural-horticultural insecticide, miticide or fungicide, its suitable dosage is usually 5 to 5000 g per 10 ares. When it is formulated into a wettable powder or emulsifiable concentrate and used after dilution with water, the concentration of the compound of the invention to be applied is 10 ppm to 1000 ppm. When it is formulated into a dust, a granular composition or an oil, it is used directly without dilution.

When a compound of this invention is to be used as an industrial fungicide, it may be directly incorporated into industrial products or materials to be protected, for example fibrous products (especially spun products containing cellulose, viscose, etc.), materials having a synthetic resin such as a polyamide or polyvinyl chloride as a base, paints and lacquers containing casein, etc., inorganic or organic pigments, pastes made from starch or cellulose derivatives, viscous animal materials, and oils.

The compounds of this invention can also be used as a spray or a dry cleaner, or as an organic solvent solution for wood impregnation. They can also be used as emulsifiers. Furthermore, the compounds of this invention may be used in the form of aqueous suspensions together with wetting or dispersing agents for protecting perishable materials, such as leather and paper.

Preferably, the compounds of this invention are used for disinfection of washed products, and protecting such products from microbial attack. For this purpose, it is desirable to use them as washing liquids in concentrations of, for example, 0.1 to 500 ppm.

When the compounds of this invention are to be used as antifouling agents, they can be incorporated in oil-type or synthetic resin-type vehicles, for example boil oils such as linseed oil, hemp seed oil and tung oil, and synthetic resin-type vehicles such as vinyl resins, alkyd resins, acrylic resins, urethane resins, synthetic rubbers and chlorinated polyethylene. The antifouling agent in accordance with this invention may be produced by using additives depending upon the purpose of their application, such as pigments, extender pigments, dyes, plasticizers, rosin and tar pitch. Or they can be produced by diluting or dissolving the compounds of this invention in organic solvents such as hydrocarbons, halogenated hydrocarbons, ketones and esters. The concentration of the compounds of this invention may be selected according to the purpose of antifouling, but is preferably at least about 1% by weight based on the entire solids.

The following examples illustrate the present invention more specifically. All parts in these examples are by weight.

EXAMPLE 1

Production of compound No. 2 of the invention (first process)

A 200 cc four-necked flask equipped with a stirrer, a thermometer, and an azeotropic dehydrator having a reflux condenser was charged with 2.35 g (0.01 mole) of 1-(2-mercaptoethyl)silatrane, 3.67 g (0.01 mole) of triphenyltin hydroxide and 80 ml of toluene, and they were well dissolved. With stirring, the solution was refluxed and azeotropically dehydrated for 1 hour. The reaction mixture was hot-filtered after addition of 0.3 g of activated carbon. The filtrate was concentrated to give 5.8 g of a white solid. Recrystallization from toluene gave 5.35 g (yield 92%) of 1-(2-triphenylstannylthioethyl)silatrane as white crystals having a melting point of 190° to 192° C.

EXAMPLE 2

Production of compound No. 4 of the invention (second process)

The same reactor as used in Example 1 was charged with 2.49 g (0.01 mole) of 1-(3-mercaptopropyl)silatrane and 100 ml of toluene, and the silatrane derivative was well dissolved. With stirring, 1.93 g (0.01 mole) of a methanol solution of sodium methylate (concentration 28%) was added dropwise. Then, 20 ml of a toluene solution of 5.54 g (0.01 mole) of trineophyltin chloride was added dropwise with stirring. The mixture was heated at 100° C. for 30 minutes to complete the reaction. The sodium chloride formed was removed by hot filtration. The filtrate was concentrated to give 7.7 g of a white solid. Recrystallization from ethanol gave 6.8 g (yield 89%) of 1-(3-trineophylstannylthiopropyl)silatrane as white crystals having a melting point of 104° to 106° C.

EXAMPLE 3

Production of compound No. 9 of the invention (third process)

A 300 cc four-necked flask equipped with a stirrer, a thermometer and an azeotropical dehydrator having a reflux condenser was charged with 1.96 g (0.01 mole) of 3-mercaptopropyltrimethoxysilane and 100 ml of toluene, and the silane compound was well dissolved. With stirring, solution of 3.67 g (0.01 mole) of triphenyltin hydroxide in 50 ml of toluene as added dropwise, and the mixture was azeotropically dehydrated to synthesize triphenyltin thiopropyltrimethoxysilane. The reaction mixture was then cooled, and 1.91 g (0.01 mole) of triisopropanolamine and 0.05 g of potassium hydroxide were added. While the mixture was stirred at 50° to 70° C. for 2 hours, the resulting methanol was removed as an azeortrope with toluene. After hot filtration, the filtrate was concentrated to give 6.3 g of a white solid. Recrystallization from a mixture of ethanol and toluene gave 5.1 g (yield 79%) of 1-(3-triphenylstannylthiopropyl)-3,7,10-trimethylsilatrane as white crystals having a melting point of 153.5° to 154.0° C.

EXAMPLE 4

Table 1 gives some examples of the compounds of this invention which can be produced by the first to third processes in the same way as described in Examples 1 to 3.

TABLE 1

$$(R^1)_3SnS(CH_2)_mSi\underset{\underset{OCHCH_2}{|}}{\overset{\overset{OCHCH_2}{|}}{\underset{R^4}{\overset{R^2}{\diagdown}}}}\underset{}{\overset{}{\diagup}}N$$

| Compound No. | $R^1$ | $R^2$ | $R^3$ | $R^4$ | m | Process | Physical property |
|---|---|---|---|---|---|---|---|
| 1 | 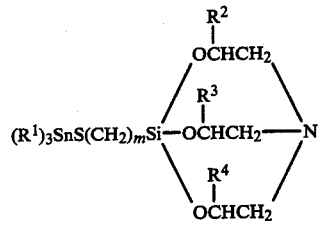 | H | H | H | 3 | first | m.p. 135–137° C. |
| 2 | 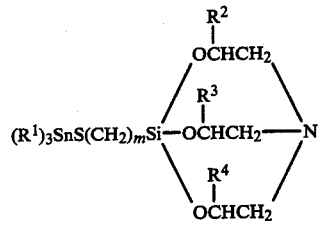 | H | H | H | 2 | " | m.p. 190–192° C. |
| 3 | 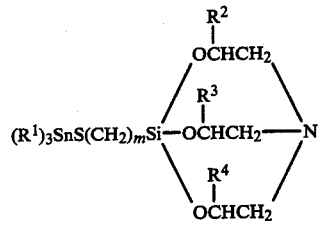 | CH$_3$ | CH$_3$ | CH$_3$ | 2 | " | m.p. 142–146° C. |

TABLE 1-continued $$(R^1)_3SnS(CH_2)_mSi\begin{matrix}R^2\\|\\OCHCH_2\\R^3\\|\\-OCHCH_2-N\\R^4\\|\\OCHCH_2\end{matrix}$$

| Compound No. | R¹ | R² | R³ | R⁴ | m | Process | Physical property |
|---|---|---|---|---|---|---|---|
| 4 | 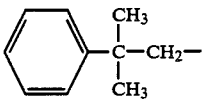 | H | H | H | 3 | second | m.p. 104–106° C. |
| 5 | 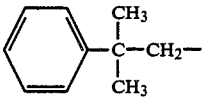 | H | H | H | 2 | first | m.p. 107–110° C. |
| 6 | 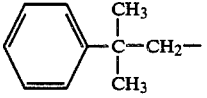 | $CH_3$ | $CH_3$ | $CH_3$ | 2 | second | $n_D^{30}$ 1.5639 |
| 7 | 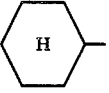 | H | H | H | 2 | first | m.p. 150.5–152° C. |
| 8 | n-$C_4H_9$— | $CH_3$ | $CH_3$ | $CH_3$ | 2 | " | $n_D^{30}$ 1.5066 |
| 9 | 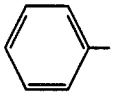 | $CH_3$ | $CH_3$ | $CH_3$ | 3 | third | m.p. 153.5–154° C. |
| 10 | 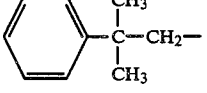 | $CH_3$ | $CH_3$ | $CH_3$ | 3 | first | $n_D^{30}$ 1.5687 |
| 11 | 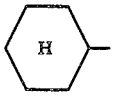 | $CH_3$ | $CH_3$ | $CH_3$ | 3 | " | $n_D^{30}$ 1.5438 |
| 12 | n-$C_4H_9$— | $CH_3$ | $CH_3$ | $CH_3$ | 3 | third | $n_D^{30}$ 1.5083 |
| 13 | 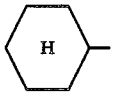 | H | H | H | 3 | first | m.p. 145–147° C. |
| 14 | n-$C_4H_9$— | H | H | H | 3 | " | $n_D^{30}$ 1.5222 |
| 15 | n-$C_8H_{17}$— | H | H | H | 3 | " | $n_D^{30}$ 1.5052 |
| 16 | n-$C_8H_{17}$— | $CH_3$ | $CH_3$ | $CH_3$ | 3 | " | $n_D^{30}$ 1.4957 |
| 17 | n-$C_3H_7$— | H | H | H | 3 | " | $n_D^{30}$ 1.5313 |
| 18 | n-$C_3H_7$— | $CH_3$ | $CH_3$ | $CH_3$ | 3 | " | $n_D^{30}$ 1.5132 |
| 19 | n-$C_4H_9$— | H | $C_2H_5$ | $C_2H_5$ | 3 | " | $n_D^{30}$ 1.5090 |
| 20 | 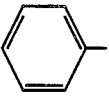 | H | $C_2H_5$ | $C_2H_5$ | 3 | " | m.p. 98.5–100.5° C. |

TABLE 1-continued $$(R^1)_3SnS(CH_2)_mSi\begin{matrix}OCHCH_2\\|\\R^2\end{matrix}\begin{matrix}R^3\\|\\OCHCH_2\\|\\R^4\\OCHCH_2\end{matrix}N$$

| Compound No. | R¹ | R² | R³ | R⁴ | m | Process | Physical property |
|---|---|---|---|---|---|---|---|
| 21 | α,α-dimethylbenzyl (PhC(CH₃)₂CH₂–) | H | C₂H₅ | C₂H₅ | 3 | " | $n_D^{30}$ 1.5697 |
| 22 | cyclohexyl (C₆H₁₁–) | H | C₂H₅ | C₂H₅ | 3 | " | $n_D^{30}$ 1.5442 |
| 23 | n-C₃H₇— | H | C₂H₅ | C₂H₅ | 3 | " | $n_D^{30}$ 1.5143 |
| 24 | n-C₄H₉— | H | H | CH₃ | 3 | " | $n_D^{30}$ 1.5156 |
| 25 | n-C₄H₉— | H | H | C₂H₅ | 3 | " | $n_D^{30}$ 1.5071 |
| 26 | iso-C₄H₉— | H | H | H | 3 | " | $n_D^{30}$ 1.5237 |
| 27 | iso-C₄H₉— | CH₃ | CH₃ | CH₃ | 3 | " | $n_D^{30}$ 1.5081 |
| 28 | iso-C₄H₉— | H | C₂H₅ | C₂H₅ | 3 | " | $n_D^{30}$ 1.5103 |
| 29 | n-C₈H₁₇— | H | H | H | 3 | " | $n_D^{30}$ 1.5049 |
| 30 | n-C₈H₁₇— | CH₃ | CH₃ | CH₃ | 3 | " | $n_D^{30}$ 1.4960 |
| 31 | phenyl (C₆H₅–) | H | H | C₂H₅ | 3 | " | m.p. 73.5–75° C. |
| 32 | phenyl (C₆H₅–) | CH₃ | CH₃ | C₂H₅ | 3 | " | m.p. 124–126° C. |
| 33 | α,α-dimethylbenzyl (PhC(CH₃)₂CH₂–) | H | H | C₂H₅ | 3 | " | $n_D^{30}$ 1.5749 |
| 34 | α,α-dimethylbenzyl (PhC(CH₃)₂CH₂–) | CH₃ | CH₃ | C₂H₅ | 3 | " | $n_D^{30}$ 1.5678 |
| 35 | cyclohexyl (C₆H₁₁–) | CH₃ | CH₃ | CH₃ | 3 | " | m.p. 156–157° C. |
| 36 | cyclohexyl (C₆H₁₁–) | H | H | C₂H₅ | 3 | second | m.p. 60–62° C. |
| 37 | cyclohexyl (C₆H₁₁–) | CH₃ | CH₃ | C₂H₅ | 3 | first | $n_D^{30}$ 1.5425 |

TABLE 1-continued $$(R^1)_3SnS(CH_2)_mSi \begin{array}{c} OCHCH_2 \\ | \\ R^2 \\ | \\ OCHCH_2 \\ | \\ R^3 \\ | \\ OCHCH_2 \\ | \\ R^4 \end{array} N$$

| Compound No. | $R^1$ | $R^2$ | $R^3$ | $R^4$ | m | Process | Physical property |
|---|---|---|---|---|---|---|---|
| 38 | CH$_3$–C(CH$_3$)(CH$_3$)–CH$_2$– | H | H | H | 2 | " | m.p. 144–146° C. |

Examples of formulation are shown below. The compound numbers correspond to those given in Table 1.

FORMULATION EXAMPLE 1

Dust

Two parts of compound No. 1 or 7 of the invention is mixed with 88 parts of clay and 10 parts of talc to give a dust.

FORMULATION EXAMPLE 2

Wettable powder

Fifty parts of each of compounds Nos. 1 to 16 of the invention, 45 parts of diatomaceous earth, 2.5 parts of calcium alkylbenzenesulfonate (wetting agent) and 2.5 parts of calcium ligninsulfonate (dispersant) are well pulverized and mixed to give a wettable powder.

FORMULATION EXAMPLE 3

Oil preparation

Each of compounds Nos. 17 to 25 of this invention (0.2 part), 1 part of xylene and 98.8 parts of kerosene are mixed to give an oil preparation.

FORMULATION EXAMPLE 4

Emulsifiable concentrate

Ten parts of each of compounds Nos. 26 to 32 of this invention, 14 parts of polyoxyethylene styryl phenyl ether, 6 parts of calcium dodecylbenzenesulfonate, 35 parts of xylene and 35 parts of dimethylformamide are well mixed to give an emulsifiable concentrate.

FORMULATION EXAMPLE 5

Wettable powder

Twenty parts of each of compounds Nos. 1 to 38 of the invention, 10 parts of Fenitrothion (a registered trademark of Sumitomo Chemical Co., Ltd.), 3 parts of calcium ligninsulfonate, 2 parts of sodium laurylsulfate and 65 parts of synthetic hydrous silicon oxide are well pulverized and mixed to give a wettable powder.

FORMULATION EXAMPLE 6

Dust

One part of compound No. 4 of the invention, 2 parts of Carbaryl (a registered trademark of Union Carbide Corporation), 87 parts of kaolin clay and 10 parts of talc are well pulverized and mixed to give a dust.

FORMULATION EXAMPLE 7

Granules

Five parts of compound No. 16 of the invention, 1 part of synthetic hydrous silicon oxide, 2 parts of calcium ligninsulfonate, 30 parts of bentonite and 62 parts of kaolin clay are well pulverized and mixed. The mixture is kneaded well by adding water, and thereafter granulated and dried to give granules.

The above formulations are used either directly or after dilution with water.

EXAMPLE 5

Test on fungicidal effect on downy mildew of grape

Sandy soil was filled in plastic pots, and seeds of grape (variety: Neomuscat) were sown, and grown for about 1 month in a greenhouse to obtain young seedlings of grape in the 2–3 leaf stage. A water dilution of an emulsifiable concentrate of a wettable powder of each of the test compounds was sprayed onto the leaves of these seedlings so that the chemical adhered fully to the surfaces of the leaves. After drying the chemical in air, a suspension of conidospores of a powdery mildew pathogen of grape (*Plasmopara viticola*) was inoculated in the seedling by spraying. The seedlings were placed for 2 days in a high humidity condition at 23° C., and subsequently cultivated for 14 days in a greenhouse kept at 20° to 25° C. to cause onset of the disease. Thereafter, the state of the disease was observed.

The degree of disease was calculated by the following method. The examined leaves were classified by indices of 0, 0.5, 1, 2 and 4 according to the degrees of appearance of lesions, and the degree of disease was calculated from the following equation.

Disease index

0: No fungus colony or lesion was noted on the surface of the leaves.

0.5: A fungus colony or a lesion was observed in an area of less than 5% on the surface of the leaves.

1: A fungus colony or a lesion was observed in an area of less than 20% on the surface of the leaves.

2: A fungus colony or a lesion was observed in an area of less than 50%.

4: A fungus colony or a lesion was observed in an area of at least 50%.

$$\text{Degree of disease (\%)} = \frac{\Sigma \left( \begin{array}{c} \text{Disease} \\ \text{index} \end{array} \right) \times \left( \begin{array}{c} \text{Number of} \\ \text{leaves} \end{array} \right)}{\left( \begin{array}{c} \text{Number of} \\ \text{leaves examined} \end{array} \right) \times 4} \times 100$$

The control index was calculated from the following equation.

$$\text{Control index (\%)} = 100 - \frac{\left( \begin{array}{c} \text{Degree of disease} \\ \text{in a treated area} \end{array} \right)}{\left( \begin{array}{c} \text{Degree of disease} \\ \text{in the non-treated} \\ \text{area} \end{array} \right)} \times 100$$

The results are shown in Table 2.

TABLE 2

| Test compound No. | Concentration of the active ingredient (ppm) | Control index (%) |
|---|---|---|
| 1 | 200 | 100 |
|   | 50 | 100 |
|   | 12.5 | 97 |
| 3 | 200 | 100 |
|   | 50 | 100 |
|   | 12.5 | 98 |
| 8 | 200 | 100 |
|   | 50 | 100 |
|   | 12.5 | 94 |
| 9 | 200 | 100 |
|   | 50 | 100 |
|   | 12.5 | 98 |
| 11 | 200 | 100 |
|   | 50 | 100 |
|   | 12.5 | 96 |
| 12 | 200 | 100 |
|   | 50 | 100 |
|   | 12.5 | 100 |
| 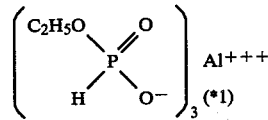 (*1) | 200 | 68 |

(*1): Commercial fungicide

EXAMPLE 6

Test on fungicidal effect on fungi

By an agar medium diluting method, the fungicidal activities of compounds Nos. 12, 17, 18, 23, 24, 26, 27 and 32 of the invention on fungi doing harm to industrial products and materials were examined.

A hypha piece, 5 mm in diameter, of each of the fungi indicated in Table 3 was inoculated in a potato dextrose agar medium (PDA) containing each of the above compounds, and cultivated at 27° C. After the lapse of a predetermined period, the growth state of the fungus was observed, and the minimum inhibitory concentration of the compound was determined. The results are shown in Table 3

TABLE 3

| | Fungus | | | | | | | |
|---|---|---|---|---|---|---|---|---|
| | Aspergillus niger ATCC 6275 | | Penicillium citrinum ATCC 9849 | | Cladosporium herbarum TAMF 517 | | Caetomium globosum ATCC 6205 | |
| Test compound No. | Cultivation period (days) | Minimum inhibitory concentration (ppm) | Cultivation period (days) | Minimum inhibitory concentration (ppm) | Cultivation period (days) | Minimum inhibitory concentration (ppm) | Cultivation period (days) | Minimum inhibitory concentration (ppm) |
| 12 | 4 | <12.5 | 4 | <12.5 | 4 | <12.5 | 3 | <12.5 |
| 17 | 4 | <2.5 | 4 | <2.5 | 4 | <12.5 | 3 | <2.5 |
| 18 | 4 | <2.5 | 4 | <12.5 | 4 | <12.5 | 4 | <12.5 |
| 23 | 4 | <2.5 | 4 | <2.5 | 4 | <2.5 | 3 | <2.5 |
| 24 | 4 | <12.5 | 4 | <12.5 | 4 | <12.5 | 3 | <12.5 |
| 26 | 4 | <12.5 | 4 | <12.5 | 4 | <12.5 | 3 | <12.5 |
| 27 | 4 | <12.5 | 4 | <12.5 | 4 | <12.5 | 3 | <12.5 |
| 32 | 4 | <12.5 | 4 | <12.5 | 4 | <12.5 | 3 | <12.5 |

EXAMPLE 7

Test on insecticidal effect on *Culex pipiens*

A wettable powder of each of compounds Nos. 2, 7, 8, 11, 13, 14, 17, 18 and 31 obtained in accordance with Formulation Example 5 was diluted with water to 3.5 ppm. One hundred milliliters of the dilution was put in each of 180 ml. polyethylene cups and 20 final-instar larvae of *Culex pipiens* were released into the cup. On the next day, the larvae were examined for mortality.

Thereafter, feeds were added to the test areas, and when all larvae n the non-treated area emerged, the emergence inhibition rate was examined.

The death rate and the emergence inhibition rate were rated by three grades as follows:

| Death rate (%) | Emergence inhibition rate (%) |
|---|---|
| A: 90% or higher | A: 90% or higher |
| B: less than 90% to 10% | B: less than 90% to 80% |
| C: less than 10% | C: less than 80% |

The results are shown in Table 4.

TABLE 4

| Test compound No. | Death rate (%) | Emergence inhibition rate (%) |
|---|---|---|
| 2 | B | A |
| 7 | C | A |
| 8 | B | A |
| 11 | B | A |
| 13 | A | A |
| 14 | A | A |
| 17 | C | A |
| 18 | B | A |
| 31 | B | A |

EXAMPLE 8

Test on insecticidal efficacy on tobacco cutworms
(*Prodenia litura* Fabrficius)

A wettable powder of each of compounds Nos. 3, 7, 8, 9, 11, 12, 13, 14, 17, 18 and 31 of the invention obtained in accordance with Formulation Example 5 was diluted with water to 200 times (corresponding to a concentration of 500 ppm). Two milliliters of the dilution was impregnated in 13 g of an artificial feed for tobacco cutworms, and the feed was put in a polyethylene cup having a diameter of 11 cm. Ten 4th-instar larvae of tobacco cutworms were released into the cup, and examined for mortality 6 days later. The above experiment was carried out through two replicates.

The results are shown in Table 5.

TABLE 5

| Test compound No. | Death rate (%) |
|---|---|
| 3 | 100 |
| 7 | 100 |
| 8 | 100 |
| 9 | 100 |
| 11 | 100 |
| 12 | 100 |
| 13 | 100 |
| 14 | 100 |
| 17 | 100 |
| 18 | 100 |
| 31 | 100 |

EXAMPLE 9

Miticidal effect on carmine mites (*Tetranychus telarius* L.)

Female imagoes of carmine mites were caused to live at a rate of 10 per leaf on bineless kidney beans (in the primary leaf stage) in pots 7 days after sowing, and kept in a constant temperature chamber at 25° C. Six days later, a chemical obtained by diluting a wettable powder of each of compounds Nos. 4–6, 9–13, 15, 16, 21, 22, 25, 28–30, 33, 34, 36, 37 and 38 with water to an active ingredient concentration of 500 ppm was sprayed at a rate of 10 ml per pot, and at the same time, 2 ml of the chemical was poured into the soil. Eight days later, injuries to the plants by the mites were examined.

The degree of injury is shown by $-$, $+$ and $++$ as follows:

$-$: Hardly any injury was observed.
$+$: Some injury was observed.
$++$: The same injury as in the non-treated area was noted.

The results are shown in Table 6.

TABLE 6

| Test compound No. | Degree of injury | Test compound No. | Degree of injury |
|---|---|---|---|
| 4 | $-$ | 22 | $--+$ |
| 5 | $--+$ | 25 | $--+$ |
| 6 | $--+$ | 28 | $-$ |
| 9 | $-$ | 29 | $--+$ |
| 10 | $-$ | 30 | $-$ |
| 11 | $-$ | 33 | $-$ |
| 12 | $-$ | 34 | $-$ |
| 13 | $-$ | 36 | $--+$ |
| 15 | $-$ | 37 | $-$ |
| 16 | $-$ | 38 | $-$ |
| 21 | $-$ | Non-treated | $++$ |

EXAMPLE 10

Test on antifouling effects on marine animals and plants in the sea

A ship bottom antifouling paint was prepared by adding 24 g of Rosin WW, 12 g of a vinyl copolymer, 4 g of tricresyl phosphate, 10 g of bentonite, 20 g of baryta, 20 g of red iron oxide, 35 g of xylene and 35 g of methyl isobutyl ketone to 40 g of each of compounds Nos. 2, 8, 14, 17, 20 and 32 of the invention and vigorously stirring the mixture at room temperature for 1 hour. The paint was coated on both surfaces of a rigid vinyl chloride resin plate, 17×9×0.3 cm in size, to a dry thickness of about 200 microns. The coated plate was submerged in the sea in Owase Bay, Mie Prefecture, Japan for 12 months, and its fouled state was regularly observed.

The results are shown in Table 7.

The symbols in the table show the following.

O: No adhesion of marine animals and plants
Δ: Marine animals and plants adhered to less than 5% of the area of the coated film
X: Marine animals and plants adhered to 5 to 20% of the area of the coated film
XX: Marine animals and plants adhered to 20 to 50% of the area of the coated film
XXX: Marine animals and plants adhered to more than 50% of the area of the coated film

TABLE 7

| Test compound No. | Period of submerging (months) | | | Fouled by |
|---|---|---|---|---|
| | 4 | 8 | 12 | |
| 2 | | | | |
| 8 | | | | |
| 14 | | | | |
| 17 | | | | |
| 20 | | | Δ | Algae |
| 32 | - | | | |
| Blank (comparison) | XXX | — | — | Algae, barnacle, and Serpulae |

What is claimed is:

1. A tri-organotin silatrane derivative represented by the general formula (I)

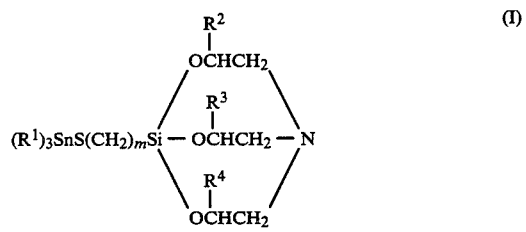

wherein $R^1$ groups are identical or different and each represents an alkyl, cycloalkyl, aryl or aralkyl group, $R^2$, $R^3$ and $R^4$ are identical or different and each represents a hydrogen atom or a lower alkyl group, and m is a number of 2 or 3.

2. The tri-organotin silatrane derivative of claim 1 wherein in formula (I), $R^1$ groups are identical or different and each represents an alkyl group having 1 to 8 carbon atoms, a cycloalkyl group having 5 to 8 carbon atoms or a phenylalkyl group having 7 to 10 carbon atoms; $R^2$, $R^3$ and $R^4$ are identical or different and each represents a hydrogen atom or a lower alkyl group having 1 to 4 carbon atoms; and m is 2 or 3.

3. The tri-organotin silatrane derivative of claim 1 wherein in formula (I), $R^1$ groups are identical or different and each represents propyl, butyl, pentyl, octyl, cyclohexyl, phenyl or 2,2-dimethyl-2-phenylethyl; $R^2$, $R^3$, $R^4$ are identical or different and each represents hydrogen, methyl or ethyl; and m is 2 or 3.

4. An agricultural-horticultural pesticidal composition comprising a pesticidally effective amount of a tri-organotin silatrane derivative represented by the general formula (I)

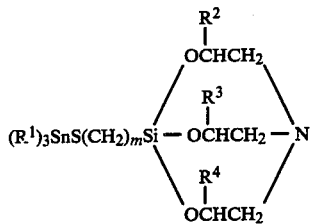

(I)

wherein $R^1$ groups are identical or different and each represents an alkyl, cycloalkyl, aryl or aralkyl group, $R^2$, $R^3$ and $R^4$ are identical or different and each represents a hydrogen atom or a lower alkyl group, and m is a number of 2 or 3,
as an active ingredient, and an inert carrier.

5. An industrial fungicide comprising a fungically effective amount of a tri-organotin silatrane derivative represented by the general formula (I)

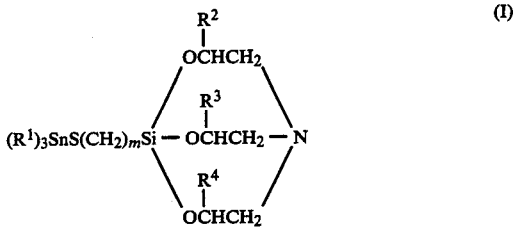

(I)

wherein $R^1$ groups are identical or different and each represents an alkyl, cycloalkyl, aryl or aralkyl group, $R^2$, $R^3$ and $R^4$ are identical or different and each represents a hydrogen atom or a lower alkyl group, and m is a number of 2 or 3, as an active ingredient.

6. An epidemic-preventing insecticide comprising an insecticidally effective amount of a tri-organotin silatrane derivative of general formula (I) as an active ingredient.

7. An antifouling agent comprising in antifouling effective amount of a silatrane derivative represented by general formula (I) as an active ingredient, and a vehicle.

* * * * *